(12) United States Patent
Ooya et al.

(10) Patent No.: US 8,268,968 B2
(45) Date of Patent: Sep. 18, 2012

(54) METHOD FOR PRODUCING MODIFIED BIOPOLYMER AND METHOD FOR CROSSLINKING BIOPOLYMER

(75) Inventors: Shouji Ooya, Kanagawa (JP); Tetsuo Hiratou, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 161 days.

(21) Appl. No.: 12/519,104

(22) PCT Filed: Dec. 13, 2007

(86) PCT No.: PCT/JP2007/001392
§ 371 (c)(1),
(2), (4) Date: Jun. 12, 2009

(87) PCT Pub. No.: WO2008/072379
PCT Pub. Date: Jun. 19, 2008

(65) Prior Publication Data
US 2010/0087626 A1    Apr. 8, 2010

(30) Foreign Application Priority Data

Dec. 13, 2006   (JP) .................................. 2006-335274
Feb. 21, 2007   (JP) .................................. 2007-040467

(51) Int. Cl.
*C07K 14/78*   (2006.01)
*C07K 1/107*   (2006.01)
*C12P 1/00*   (2006.01)

(52) U.S. Cl. ........... 530/354; 530/402; 536/124; 435/41

(58) Field of Classification Search ............ 530/354, 530/402; 536/124; 435/41
See application file for complete search history.

(56) References Cited

U.S. PATENT DOCUMENTS

2007/0077274 A1 *   4/2007   Ahlers .......................... 424/423

FOREIGN PATENT DOCUMENTS

| | | |
|---|---|---|
| EP | 1 483 963 A1 | 12/2004 |
| FR | 2 659 352 A1 | 9/1991 |
| JP | 52-125613 A | 10/1977 |
| JP | 03-259927 A | 11/1991 |
| JP | 4-222559 A | 8/1992 |
| JP | 06-098743 A | 4/1994 |
| JP | 10-265590 A | 10/1998 |
| JP | 2002-531182 A | 9/2002 |
| JP | 2004-339395 A | 12/2004 |
| JP | 2007-224012 A | 9/2007 |
| WO | 94/27630 A1 | 12/1994 |
| WO | 00/32251 A1 | 6/2000 |
| WO | 2005/111121 A2 | 11/2005 |

OTHER PUBLICATIONS

Yamamda et al. (1994), English translation of JP-06-098743 (machine translation).*
Jiyoukiyuu et al. JP 10-265590 (published on 1998), English translation (Machine translation).*
An English-language International Preliminary Report on Patentability dated Jun. 25, 2009.
Extended European Search Report dated Jun. 8, 2012 on European Application No. EP 07 84 9825.

* cited by examiner

*Primary Examiner* — Chih-Min Kam
(74) *Attorney, Agent, or Firm* — Sughrue Mion, PLLC

(57) ABSTRACT

It is an object of the present invention to provide a method wherein a structure which was prepared with a biopolymer such as gelatin is chemically modified with the use of a low-volatile chemical substance without dissolution of gelatin, and a biopolymer crosslinking method for producing a biopolymer having high strength (a high degree of crosslinking). The present invention provides a method for producing a modified biopolymer, which comprises reacting a structure prepared with a biopolymer with a solid-state compound having a melting point of 50° C. or more at a humidity of 50% or more, and a method for crosslinking biopolymer which comprises treating a biopolymer with a crosslinking agent, wherein the crosslinking agent concentration in a reaction mixture is 1.0% to 10% by weight and crosslinking is carried out in the presence of an organic fluorine compound.

9 Claims, No Drawings

METHOD FOR PRODUCING MODIFIED BIOPOLYMER AND METHOD FOR CROSSLINKING BIOPOLYMER

CROSS-REFERENCE TO RELATED APPLICATIONS

The present application is a U.S. National Stage entry of PCT/JP2007/001392 filed Dec. 13, 2007 and claims priority to Japanese Patent Application Nos. 335274/2006 filed Dec. 13, 2006 and 040467/2007 filed Feb. 21, 2007. The contents of these three related applications are incorporated herein by reference in their entireties.

TECHNICAL FIELD

The present invention relates to a method for producing a modified biopolymer which comprises causing a chemical reaction between a structure prepared with a biopolymer and a compound in a solid state at a high humidity. Further, the present invention relates to a method for crosslinking biopolymer.

BACKGROUND ART

Each of biopolymers has specific biological active property. Therefore, they are expected to be used as elemental materials for regenerative medicine and drug delivery systems. However, many biopolymers themselves are water soluble at physiological temperatures. Therefore, in order to use biopolymers for medicine, they are chemically modified with a low molecular compound or are crosslinked. In general, chemical modification of biopolymers is carried out by a method involving a chemical reaction in a solution for forming/processing or a method wherein a preliminarily prepared structure is immersed in a solution containing a compound (e.g., a crosslinking agent) that can cause chemical modification.

Meanwhile, in recent years, electrospinning has been gaining attention as a technique for readily producing submicron-scale fibers. In the case of such technique, fibers are formed by injecting a polymer solution while applying a voltage to the solution. The fiber thickness depends on applied voltage, solution concentration, and the distances that sprayed particles move. A thin film having a three-dimensional structure (three-dimensional mesh structure) can be obtained by continuously forming fibers on a substrate. In addition, a film having a fabric-like thickness can be produced by the aforementioned method, and a non-woven fabric having a submicron-scale mesh structure can be produced. Applied use of such non-woven fabric for spacesuits and protective suits is being studied. The above technique is used for formation of a structure used in the field of medicine with the use of biopolymers (JP Patent Publication (Kohyo) No. 2004-532802 A and JP Patent Publication (Kokai) No. 2004-321484 A).

JP Patent Publication (Kohyo) No. 2004-532802 A describes that a collagen structure which was preliminarily prepared by electrospinning is exposed to a glutaraldehyde vapor so that the structure is crosslinked. However, such technique involves crosslinking merely caused by exposing a collagen structure to a volatile glutaraldehyde gas. Glutaraldehyde has been widely used as a crosslinking agent for collagen and gelatin. However, glutaraldehyde itself is toxic. In addition, a glutaraldehyde-derived structure is introduced in the obtained crosslinked structure. Therefore, there is a possibility to lose useful characteristics inherent in collagen or gelatin. In addition, there is a possibility that the structure could become unexpectedly toxic.

Meanwhile, there is a method for crosslinking collagen and gelatin with an enzyme. A known enzyme used for crosslinking collagen and gelatin is transglutaminase. Transglutaminase is an enzyme that allows glutamine residues and lysine residues to bond with each other. In general, an enzyme exhibits activity specifically at an optimum temperature, and it exhibits significantly lowered activity at a non-optimum temperature (e.g., Activa TG-S, produced by Ajinomoto Co., Inc. with an optimum temperature of approximately 50° C.). Crosslinking of gelatin with transglutaminase normally takes place at 30° C. to 60° C., at which gelatin can be dissolved in water. Therefore, when crosslinking is caused with the use of transglutaminase without dissolution of a structure comprising gelatin, it is necessary to cause a reaction at 20° C. or less at which gelatin is not dissolved in water (JP Patent No. 3012743). However, when a structure comprising gelatin is immersed in water at a low temperature, a structure might become significantly deformed, which is problematic. In such case, it would be difficult to cause efficient crosslinking while preventing deformation of a preliminarily prepared gelatin structure.

In addition, biopolymers, which are biologically derived polymers, have specific physiological and biological properties and therefore they are frequently used for medical and biological purposes. However, since biopolymers are generally water soluble, they lack the physical strength that is necessary for chemical modification or crosslinking when used in a solid form. In view of the above, biopolymers are coated to synthetic polymers and inorganic substances (Brash, Trans. Am. Soc. Artif. Int. Organs, p. 69, 1974), or hybrid products (composites) are formed with such materials and biopolymers. However, in consideration of biological safety, materials consisting of biopolymers only are preferably used.

For improvement of biodegradability and strength of a biopolymer and water insolubility of a biopolymer, a technique of chemically modifying a partial functional group of a biopolymer and a technique of crosslinking between biopolymers have been devised. In particular, crosslinking between biopolymers has been actively studied. For instance, crosslinking of gelatin with the use of glutaraldehyde or a condensation agent has been widely carried out. It is reported that this method is effective in the field of regenerative medicine and in the drug delivery field (JP Patent No. 3639593). However, the degree of crosslinking and the strength achieved by such crosslinking are insufficient. Therefore, applied use of biopolymers for medical purposes is limited.

For crosslinking of gelatin, a method for crosslinking gelatin with glutaraldehyde is generally used. In this method, it is necessary to carry out stirring at a temperature at which gelatin can be dissolved (i.e., 30° C. or more). However, the reactivity of gelatin and glutaraldehyde becomes high at such temperature. As a result, it becomes impossible to uniformly stir the entire solution. In such case it is impossible to use a crosslinking agent at a high concentration. Thus, it has been difficult to produce gelatin having a high degree of crosslinking. Accordingly, it has been difficult to produce gelatin having a high strength and a high degree of crosslinking.

JP Patent Publication (Kohyo) No. 2002-531182 A describes that a matrix for tissue construction that comprises a protein is produced by dissolving the protein and alkyl ester of hyaluronate in HFIP, followed by forming. In addition, JP Patent Publication (Kohyo) No. 2004-532802 A and JP Patent Publication (Kokai) No. 2004-321484 A describe that a protein structure is produced by electrospinning. However, in these methods, crosslinking is not carried out in HFIP. In addition, there is an example involving crosslinking of fibers with the use of glutaraldehyde, such fibers being produced by electrospinning using HFIP as a solvent (Biomaterials, 27(8), 452-1461, 2006). However, this method merely involves crosslinking of a prepared structure with the use of a glutaraldehyde vapor.

DISCLOSURE OF THE INVENTION

Object to be Solved by the Invention

It is an object of the present invention to solve the above problems of conventional techniques. That is, it is an object of the present invention to provide a method wherein a structure which was prepared with a biopolymer such as gelatin is chemically modified with the use of a low-volatile chemical substance without dissolution of gelatin. It is another object of the present invention to provide a biopolymer crosslinking method for producing a biopolymer such as gelatin having high strength (a high degree of crosslinking), which has been difficult to produce by conventional techniques.

Means for Solving the Object

As a result of intensive studies in order to achieve the above objects, the present inventors have found that a modified biopolymer can be produced by allowing a structure prepared with a biopolymer to react with a solid-state compound having a melting point of 50° C. or more at a high humidity. This has led to the completion of the present invention. Further, the present inventors have conducted intensive studies to achieve the above objects. As a result, they have found that a biopolymer having a high strength (a high degree of crosslinking) can be produced by adjusting the concentration of a crosslinking agent in a reaction mixture to 1.0% to 10% by weight and performing crosslinking in the presence of an organic fluorine compound, when a biopolymer is treated with the crosslinking agent. This has led to the completion of the present invention.

The present invention provides a method for producing a modified biopolymer, which comprises reacting a structure prepared with a biopolymer with a solid-state compound having a melting point of 50° C. or more at a humidity of 50% or more.

Preferably, the compound having a melting point of 50° C. is a crosslinking agent.

Preferably, the crosslinking agent is a condensation agent or an enzyme.

Preferably, the crosslinking agent is 1-ethyl-3-(3-dimethylaminopropyl)carbodiimide or transglutaminase.

Preferably, the biopolymer is a protein or polysaccharide (e.g., glycosaminoglycan or proteoglycan).

Preferably, the biopolymer comprises at least one protein selected from the group consisting of collagen, gelatin, albumin, laminin, casein, fibroin, fibrin, chitosan, fibronectin, and vitronectin.

Preferably, the protein is a human-, bovine-, pig-, or fish-derived protein, or a gene recombinant protein.

Preferably, the structure prepared with a biopolymer contains an additive.

The present invention further provides a method for crosslinking biopolymer which comprises treating a biopolymer with a crosslinking agent, wherein the crosslinking agent concentration in a reaction mixture is 1.0% to 10% by weight and crosslinking is carried out in the presence of an organic fluorine compound.

Preferably, the temperature for mixing before reaction is 0° C. to 30° C.

Preferably, the temperature for mixing before reaction is 0° C. to 25° C.

Preferably, the biopolymer contains at least one selected from the group consisting of a protein, a polysaccharide, and a derivative thereof.

Preferably, the biopolymer is a protein.

Preferably, the protein comprises at least one selected from the group consisting of collagen, gelatin, albumin, laminin, casein, fibroin, fibrin, fibronectin, vitronectin, urokinase, thrombomodulin, and antithrombin III.

Preferably, the protein is a human-, bovine-, pig-, fish-, or plant-derived protein, or a gene recombinant protein.

Preferably, the crosslinking agent is aldehyde, a condensation agent, or an enzyme.

Preferably, the crosslinking agent is aldehyde.

Preferably, the crosslinking agent is glutaraldehyde.

Preferably, the organic fluorine compound has a carbon number of 1 to 8.

Preferably, the organic fluorine compound is alcohol, ketone, or carboxylic acid.

Preferably, the organic fluorine compound is 1,1,1,3,3,3-hexafluoro-2-propanol, 2,2,2-trifluoroethanol, hexafluoroacetone, trifluoroacetic acid, or pentafluoro propionic acid.

Preferably, the organic fluorine compound is 1,1,1,3,3,3-hexafluoro-2-propanol or 2,2,2-trifluoroethanol.

Another aspect of the present invention provides a method for producing a crosslinked biopolymer, which comprises the method of the present invention as mentioned above.

Another aspect of the present invention provides a crosslinked gelatin composition, which has a Young's modulus of 200 KPa or more.

Preferably, there is provides a crosslinked gelatin composition, which has a Young's modulus of 300 KPa or more.

Preferably, a crosslinking agent used for the crosslinked gelatin is glutaraldehyde.

Preferably, the gelatin is acid-treated gelatin.

Effect of the Invention

According to the present invention, it is possible to minimize the amount of a solvent used during chemical modification operations. Therefore, it is possible to cause crosslinking without dissolving a composite prepared with a biopolymer in a solvent. Accordingly, it is possible to maintain the form of a composite prepared with a biopolymer by means of the method of the present invention. Further, it is possible to prevent and minimize elution of a pharmaceutical agent that has been added during chemical modification operations.

In addition, implementation of the present invention facilitates: (1): a reaction that is more efficient than that caused in an aqueous system; and (2): handling upon the use of a reagent having high reactivity and a matrix such as gelatin that is formed into a gel at a low temperature in an aqueous solution. As a result, a crosslinked biopolymer having a high degree of strength can be produced.

BEST MODE FOR CARRYING OUT THE INVENTION

Hereinafter, the present invention is described in greater detail.
(1) Method for Producing a Modified Biopolymer A biopolymer to be used in the present invention is not particularly limited, as long as it is a biologically derived polymer, and it is preferably a protein, a saccharide or a derivative thereof. More preferably, the biopolymer is collagen, gelatin, albumin, laminin, casein, fibroin, fibrin, chitosan, fibronectin, vitronectin, or hyaluronic acid ester (hyaluronate). Further preferably, the biopolymer is collagen, gelatin, albumin, casein, or fibroin. Most preferably, the biopolymer is collagen or gelatin. When the biopolymer is a protein, the protein origin is not particularly limited. Any human-, bovine-, pig-, or fish-derived proteins or gene recombinant proteins can be used. As a gene recombinant gelatin, those described in EU 1014176A2 or U.S. Pat. No. 6,992,172 can be used, but the examples are not limited thereto.

The form of the biopolymer is not particularly limited. However, the biopolymer may be in the form of a non-crosslinked product, a physically or chemically crosslinked product, a chemically modified product, or a mixture thereof. In addition, it is not required that the biopolymer be present alone within a structure prepared with the use of the biopolymer, and the biopolymer may be contained as a partial component in the structure.

The structure prepared with the use of the biopolymer is usually a solid. The form of the structure is not particularly limited, and examples of the form include gel, sponge, film, non-woven fabric, fibers (tubes), and particles. The structure can be used in any form. Examples of such form include pyramidal, conical, rectangular cylindrical, circular cylindrical, spherical, and spindle-shaped structure, and structure produced by using molds with any desired shapes. Preferably, the form is a rectangular cylindrical, circular cylindrical, or spindle-shaped structure, or a structure produced using a mold with any desired shape. More preferably, the form is a pyramidal, conical, rectangular cylindrical, or circular cylindrical structure. Most preferably, the form is a rectangular cylindrical or circular cylindrical structure.

The size of the structure is not particularly limited. When the structure is in the form of gel, sponge or non-woven fabric, the size is preferably 500 centimeters square or less, preferably 100 centimeters square or less, particularly preferably 50 centimeters square or less, and most preferably 10 centimeters square or less. When it is formed into a fiber (tube), the diameter of a fiber or tube (or one side of the cross section thereof) is 1 nm or more and 10 cm or less, preferably 1 nm or more and 1 cm or less, more preferably 1 nm or more and 100 μm or less, particularly preferably 1 nm or more and 1 μm or less, and most preferably 1 nm or more and 10 nm or less. In addition, the length thereof is not particularly limited. The length thereof is preferably 10 μm or more and 100 m or less, more preferably 100 μm or more and 10 m or less, further preferably 1 mm or more and 1 m or less, and most preferably 1 cm or more and 30 cm or less. When the structure is in the form of particles, the particle size (diameter) preferably ranges from 1 nm to 1 mm, more preferably ranges from 10 nm to 200 μm, further preferably ranges from 50 nm to 100 μm, and particularly preferably ranges from 100 nm to 10 μm.

The thickness of the structure is not particularly limited. The thickness is preferably 1 nm or more, more preferably 10 nm or more, further preferably 100 nm or more, even more preferably 1 μm or more, yet more preferably 10 μm or more, and most preferably 100 μm or more.

In the present invention, a composite prepared with a biopolymer is allowed to react with a solid-state compound having a melting point of 50° C. or more.

The melting point of a compound used in the present invention is 50° C. or more and preferably 100° C. or more. In addition, the vapor pressure of a compound used in the present invention at 20° C. is preferably 1.5 KPa or less. In addition, the boiling point of a compound used in the present invention is preferably 200° C. or more.

Preferably, the compound having a melting point of 50° C. or more used in the present invention is a water soluble substance. More preferably, it is a chemical substance that reacts with a hydroxyl group, an amino group, or a carboxyl group. Further preferably, it is a condensation agent (e.g., carbodiimide), an enzyme, or N-hydroxysuccinimide (NHS). Even more preferably, it is a water soluble carbodiimide (1-ethyl-3-(3-dimethylaminopropyl)carbodiimide (WSC)), dicyclohexylcarbodiimide (DCC), or an enzyme. Yet more preferably, it is an enzyme. Most preferably, it is transglutaminase. In addition, a compound that is allowed to act on a structure may be a compound used for chemical modification alone or in a mixture of such a compound and a different another compound. For instance, in addition to WSC, dodecylamine may be added to a gelatin structure such that a dodecyl group can be introduced into the gelatin structure.

According to the present invention, a structure is allowed to react with a solid-state compound at a humidity of 50% or more. The humidity is not particularly limited as long as it is 50% or more. However, it is preferably 60% or more, more preferably 70% or more, and particularly preferably 80% or more. Further, a reaction system may contain a gas of a solvent other than water. In addition, the temperature in a system is not particularly limited. However, it is preferably 25° C. to 200° C., more preferably 30° C. to 100° C., and most preferably 35° C. to 80° C. When an enzyme is used, it is particularly desirable to set the temperature to a level at which enzyme activity is observed.

According to the present invention, it is possible to produce a modified biopolymer by allowing a structure to react with a solid-state compound at a humidity of 50% or more. Herein, biopolymer modification can be carried out by a chemical binding reaction between a biopolymer and a low-molecular compound or an intramolecular crosslinking reaction in a biopolymer. More preferably, an intramolecular crosslinking reaction is carried out. An intramolecular crosslinking reaction can be carried out with the use of a condensation agent or an enzyme.

A composition produced in the present invention may contain additives according to need. Examples of additives include drugs, pigments, softening agents, transdermal-absorption-promoting agents, moisturizing agents, surfactants, preservatives, aroma chemicals, and pH adjusters. Examples of drugs include anticancer agents, immunosuppressive agents, anti-inflammatory agents, antithrombotic agents, antipsychotic agents, antidepressants, growth factors, hormones, supplement components, and cosmetic components.

Applications of the above composition are not particularly limited. However, it can be used for transdermally absorbable agents, topical therapeutic agents, adhesive skin patches, liniments, oral therapeutic agents, cosmetics, supplements, foods, and pigments. Preferably, it can be used for transdermally absorbable agents, topical therapeutic agents, oral therapeutic agents, and cosmetics. Further preferably, it can be used for transdermally absorbable agents, topical therapeutic agents, adhesive skin patches, liniments, oral therapeutic agents. Most preferably, it can be used for transdermally absorbable agents and topical therapeutic agents.

(2) Method for Crosslinking Biopolymer

The method for crosslinking biopolymer according to the present invention comprises treating a biopolymer with a crosslinking agent, and is characterized in that the crosslinking agent concentration in a reaction mixture is 1.0% to 10% by weight, and crosslinking is carried out in the presence of an organic fluorine compound.

The biopolymer which is a biologically derived polymer is not particularly limited, so long as the present invention can be realized. The biopolymer is preferably a protein, a polysaccharide, or a derivative or salts thereof. In the case of a protein, the protein may be any of globular protein or fibrous protein. The biopolymer used in the present invention may include synthetic polypeptides. More preferably, the biopolymer is collagen, gelatin, albumin, laminin, casein, fibroin, fibrin, chitosan, fibronectin, vitronectin, urokinase, thrombomodulin, antithrombin III, and hyaluronic acid ester (hyaluronate). Further preferably, the biopolymer is collagen, gelatin, albumin, casein, or fibroin. Most preferably, the biopolymer is collagen or gelatin. The protein origin is not particularly limited. Any human-, bovine-, pig-, or fish-derived proteins or gene recombinant proteins can be used. As a gene recombinant gelatin, those described in EU 1014176A2 or U.S. Pat. No. 6,992,172 can be used, but the examples are not limited thereto. Also, the biopolymer may be partially hydrolyzed.

Types of organic fluorine compound to be used in the present invention are not particularly limited, as long as the biopolymer is dissolved. The organic fluorine compound is preferably a C1-8 organic fluorine compound, more preferably a C1-6 organic fluorine compound, and further more preferably a C1-3 organic fluorine compound. Preferably, the organic fluorine compound is alcohol, ketone, or carboxylic acid. Particularly preferably, the organic fluorine compound is 1,1,1,3,3,3-hexafluoro-2-propanol (HFIP), 2,2,2-trifluoroethanol (TFE), hexafluoroacetone, trifluoroacetic acid, or pentafluoropropionic acid. Most preferably, the organic fluorine compound is 1,1,1,3,3,3-hexafluoro-2-propanol or 2,2,2-trifluoroethanol. The organic fluorine compound may be used alone or may be used in combination with a solvent compatible therewith. The content of the organic fluorine compound is not particularly limited, and is preferably 0.0001% or more, more preferably 0.1% or more, further preferably 10% or more, further preferably 50% or more, and most preferably 80% or more.

A crosslinking agent used in the present invention is not particularly limited as long as the present invention can be carried out. It may be a chemical crosslinking agent or an enzyme. Examples of a chemical crosslinking agent include formaldehyde, glutaraldehyde, carbodiimide, and cyanamide. Preferably, formaldehyde and glutaraldehyde can be used. It is desirable to use a solvent that is less nucleophilic than water for protein crosslinking. Although HFIP and TFE are alcohols, they have highly acidic hydroxyl groups and are poorly nucleophilic. Therefore, it is thought that such a solvent is less likely to inhibit a reaction involving nucleophilic attack.

In a case in which enzymatic crosslinking is carried out, an enzyme used is not particularly limited as long as it has a biopolymer crosslinking action. However, crosslinking can be carried out preferably using transglutaminase or laccase and most preferably using transglutaminase. Examples of proteins that are enzymatically crosslinked by transglutaminase are not particularly limited, so ling as the protein has a lysine residue and a glutamine residue. A mammalian-derived or microorganism-derived transglutaminase may be used. Specific examples thereof include: the Activa series (produced by Ajinomoto Co., Inc.); commercially available mammalian-derived transglutaminases serving as reagents such as guinea pig liver-derived transglutaminase, goat-derived transglutaminase, and rabbit-derived transglutaminase (produced by Oriental Yeast Co., Ltd., Upstate USA Inc., Biodesign International, etc.); and a human-derived blood coagulation factor (Factor XIIIa, Haematologic Technologies, Inc.).

According to the present invention, the concentration of a crosslinking agent in a reaction mixture containing a biopolymer, an organic fluorine compound, and a crosslinking agent is 1.0% to 10% by weight and preferably 1.0% to 5.0% by weight.

Crosslinking of a biopolymer involves two steps of: mixing a biopolymer solution with a crosslinking agent; and causing a reaction of the obtained homogenous solution.

In the present invention, the temperature for mixing a biopolymer with a crosslinking agent for treatment is not particularly limited as long as the obtained solution can be uniformly stirred. However, the temperature is preferably 0° C. to 40° C., more preferably 0° C. to 30° C., further preferably 3° C. to 25° C., even more preferably 3° C. to 15° C., yet more preferably 3° C. to 10° C., and particularly preferably 3° C. to 7° C.

After stirring a biopolymer and a crosslinking agent, it is possible to raise the temperature. The reaction temperature is not particularly limited as long as crosslinking proceeds. However, in view of biopolymer degeneration or degradation, the reaction temperature is substantially 0° C. to 60° C., preferably 0° C. to 40° C., more preferably 3° C. to 25° C., further preferably 3° C. to 15° C., even more preferably 3° C. to 10° C., and particularly preferably 3° C. to 7° C.

The form of the structure of a crosslinked biopolymer which is obtained by the present invention is not particularly limited. Examples of the form include sponge, film, non-woven fabric, fibers (tubes), and particles. The structure can be used in any form. Examples of such form include pyramidal, conical, rectangular cylindrical, circular cylindrical, spherical, and spindle-shaped structure, and structure produced by using molds with any desired shapes. Preferably, the form is a rectangular cylindrical, circular cylindrical, or spindle-shaped structure, or a structure produced using a mold with any desired shape. More preferably, the form is a pyramidal, conical, rectangular cylindrical, or circular cylindrical structure. Most preferably, the form is a rectangular cylindrical or circular cylindrical structure. Further, the composition may be covered with various forms of sheets, such as waterproof sheets, depending on applications. Such sheets can comprise polyethylene, polypropylene, poly(vinylidene chloride), or the like.

The size of the structure is not particularly limited. When the structure is in the form of sponge or non-woven fabric, the size is preferably 500 centimeters square or less, preferably 100 centimeters square or less, particularly preferably 50 centimeters square or less, and most preferably 10 centimeters square or less. When it is formed into a fiber (tube), the diameter of a fiber or tube (or one side of the cross section thereof) is 1 nm or more and 10 cm or less, preferably 1 nm or more and 1 cm or less, more preferably 1 nm or more and 100 µm or less, particularly preferably 1 nm or more and 1 µm or less, and most preferably 1 nm or more and 10 nm or less. In addition, the length thereof is not particularly limited. The length thereof is preferably 10 µm or more and 100 m or less, more preferably 100 µm or more and 10 m or less, further preferably 1 mm or more and 1 m or less, and most preferably 1 cm or more and 30 cm or less. When the structure is in the form of particles, the particle size (diameter) preferably ranges from 1 nm to 1 mm, more preferably ranges from 10 nm to 200 µm, further preferably ranges from 50 nm to 100 µm, and particularly preferably ranges from 100 nm to 10 µm.

The thickness of the structure is not particularly limited. The thickness is preferably 1 nm or more, more preferably 10 nm or more, further preferably 100 nm or more, even more preferably 1 µm or more, yet more preferably 10 µm or more, and most preferably 100 µm or more.

Also, a mixture of the above biopolymer and a different synthetic polymer can be used. Such a synthetic polymer is not particularly limited as long as it can be dissolved in an organic fluorine compound. However, preferable examples thereof include a polymer having urethane bonds, ester bonds, ether bonds or carbonate bonds, vinyl polymers, and copolymers thereof. More preferable examples thereof include: polylactic acid, polyglycolic acid, and copolymers thereof; poly(ε-caprolactone), polyurethane, segmented polyurethane, polyethyleneterephthalate (PET), polymethylenecarbonate, polyvinylpyrrolidone (PVP), polyhydroxy alkanoate (PHA), glycerol, polyethyleneglycol, benzyl ester hyaluronate, ethylester hyaluronate, and acetylcellulose. Further preferable examples thereof include poly(ε-caprolactone), polyurethane, polyetherpolyurethane, segmented polyurethane, and PET.

The molecular weight of the synthetic polymer is not particularly limited. However, it is substantially 1 KDa to 10 MDa, preferably 5 KDa to 500 KDa, and most preferably 10 KDa to 100 KDa. Further, the synthetic polymer may be crosslinked and chemically modified.

Proteins such as collagen and gelatin can be dissolved in organic fluorine compounds represented by 1,1,1,3,3,3-hexafluoro-2-propanol (HFIP) and 2,2,2-trifluoroethanol (TFE). In addition, even when an HFIP solution containing gelatin, for example, is maintained at 4° C., gel formation does not take place.

With the use of the method for causing crosslinking of a biopolymer according to the present invention, a crosslinked biopolymer can be produced. It is possible to add an additive to the crosslinked biopolymer which is produced by the method of the present invention according to need. Examples of additives include drugs, pigments, softening agents, transdermal-absorption-promoting agents, moisturizing agents, thickening agents, surfactants, preservatives, aroma chemicals, and pH adjusters.

Specific examples of drugs include anticancer agents (e.g., paclitaxel, Topotecin, taxotere, 5-fluorouracil, and cisplatin), immunosuppressive agents (e.g., Rapamycin, tacrolimus, and cyclosporine), anti-inflammatory agents, antithrombotic agents, antipsychotic agents (e.g., amitriptyline hydrochloride), antidepressants, antioxidants, antiallergic agents, growth factors (e.g., fibroblast growth factors, epithelial cell growth factors, insulin-like growth factors, transforming growth factors, vascular endothelial cell growth factors, hepatocellular growth factors, platelet-derived growth factors, nerve growth factors), hormones, supplement components, and cosmetic components.

Applications of the crosslinked biopolymer produced by the method of the present invention are not particularly limited. However, it can be used for transdermally absorbable agents, topical therapeutic agents, oral therapeutic agents, cosmetics, supplements, foods, and pigments. Preferably, it can be used for transdermally absorbable agents, topical therapeutic agents, oral therapeutic agents, and cosmetics. Further preferably, it can be used for transdermally absorbable agents, topical therapeutic agents, and oral therapeutic agents. Most preferably, it can be used for transdermally absorbable agents and topical therapeutic agents.

The crosslinked biopolymer produced by the present invention can be used for, for example, skin agents for external use that contain anticancer agents. Examples of diseases to which skin agents for external use can be applied include skin cancer, keratosis, malignant melanoma, mycosis fungoides, breast cancer, prostate cancer, uterine cancer, vaginal cancer, penile cancer, and colon cancer. Preferable examples thereof are skin cancer and keratosis.

The crosslinked biopolymer produced by the present invention can be used for materials that are implantable in biotissues. For instance, it is possible to restore a tissue by implanting a crosslinked biopolymer in which cells are embedded in a lesion site. In another embodiment, it is possible to restore a tissue by implanting a crosslinked biopolymer containing a growth factor or a different pharmaceutical agent in a biotissue.

Types of cells to be contained in the crosslinked biopolymer are not particularly limited. However, examples thereof include myelocytes, embryonic stem cells, adult stem cells, chondrocytes, osteoblasts, fibroblasts, vascular endothelial cells, vascular smooth muscle cells, cardiomyocytes, and epithelial cells.

Body parts that are required to have particular strength, to which a material that is implantable in a biotissue is applied, are bones, cartilages, hearts, blood vessels, and the like.

In another embodiment, a material that is implantable in a biotissue can be used for coating of medical products used in vivo such as artificial blood vessels, artificial organs such as artificial hearts, and stents used for blood vessel treatment. When such a material is used for a stent, the stent surface can be coated with a crosslinked biopolymer containing an anticancer agent or an immunosuppressive agent.

The strength of a crosslinked gelatin would significantly vary depending on the gelatin concentration and the degree of crosslinking. In the cases of crosslinked gelatins produced by conventional methods, gelatins are allowed to gel at low temperatures. Therefore, it is difficult to mix a high-concentration crosslinking agent with a high-concentration gelatin. The strength of a crosslinked gelatin produced in the present invention is preferably 200 KPa or more, more preferably 250 KPa or more, further preferably 300 KPa or more, even more preferably 400 KPa or more. In another embodiment, the breaking load for a crosslinked gelatin with a thickness of 4 mm is preferably 150 KPa or more, more preferably 200 KPa or more, and further preferably 300 KPa or more.

The strength of a crosslinked gelatin was determined with the use of a creep meter (produced by Yamaden Co., Ltd.) (RE2-33005B; plunger diameter: ϕ=5 mm; pushing rate: 0.1 mm/s). In order to obtain the strength of crosslinked gelatin, the Young's modulus and the breaking load of crosslinked gelatin were measured. The Young's modulus was determined based on the slope of the straight line in the low strain region (strain: 0.3 or less) determined by creating a stress-distortion curve based on the stress obtained when pushing a crosslinked gelatin. In addition, the breaking load was designated as the load determined when piercing a crosslinked gelatin with a plunger so as to rupture the crosslinked gelatin.

The present invention is hereafter described in greater detail with reference to the following examples, although the technical scope of the present invention is not limited thereto.

EXAMPLES

Example 1

Transglutaminase Crosslinking of Gelatin Film

An HFIP solution containing acid-treated gelatin (5% or 20%; PSP gelatin produced by Nippi Inc.) and paclitaxel (1 mg/mL) was coated to a polypropylene substrate (size: 20 cm×20 cm; coating thickness: 1 mm). The paclitaxel-containing gelatin film was subjected to air drying for 3 days. Thus, a paclitaxel-containing gelatin film was obtained.

A transglutaminase powder (Activa TG-S, produced by Ajinomoto Co., Inc.) (100 mg) was placed on the film (1 cm×5 cm; thickness: 100 μm) and allowed to stand under the following conditions (1), (2), or (3) for 7 days.
(1) Temperature: 50° C.; Humidity: 95%
(2) Temperature: 50° C.; Humidity: 10%
(3) Temperature: 40° C.; Humidity: 80%

The above transglutaminase has a melting point of 50° C. or above and is in a solid state at 40° C. or 50° C.

The obtained films were washed with water at 4° C., followed by drying. Thus, paclitaxel-containing gelatin films were obtained. No film experienced any obvious volume change and all remained in their original forms. The gelatin film treated under conditions (1) above (temperature: 50° C.; humidity: 95%) and the gelatin film treated under conditions (3) above (temperature: 40° C.; humidity: 80%) were immersed in water at 50° C. for 3 hours. As a result, the films were not dissolved. Further, the gelling rates of the films were measured and found to be approximately 70%. Therefore, it can be said that the films were crosslinked by transglutaminase. Meanwhile, the film treated under conditions (2) above (temperature: 50° C.; humidity: 10%) was rapidly dissolved in water at 50° C. (gelling rate: 0%).

The above results indicate that it was possible to carry out crosslinking of gelatin remaining in its original form by humidification under the presence of a solid-state crosslinking agent (i.e., transglutaminase in this Example).

Comparative Example 1

Transglutaminase Crosslinking of Gelatin Film in a Solution

The paclitaxel-containing gelatin film (3 cm×3 cm; thickness: 100 μm) used in Example 1 was immersed in a 1% transglutaminase aqueous solution (10 mL) and allowed to stand at 25° C. or 50° C. for 15 hours. The paclitaxel-containing gelatin film immersed in an aqueous solution at 25° C. became crosslinked. However, the film became swollen and thus the surface area thereof became approximately twice as large as the original surface area. Meanwhile, the paclitaxel-containing gelatin film immersed in a transglutaminase aqueous solution at 50° C. was dissolved before becoming crosslinked. Therefore, it was impossible to obtain a crosslinked film.

Example 2

Crosslinking of gelatin in 1,1,1,3,3,3-hexafluoro-2-propanol (HFIP)

The temperature of an HFIP or PBS aqueous solution containing acid-treated gelatin (PSP gelatin; produced by Nippi Inc.) at a certain concentration was set to 4° C., 25° C., or 40° C. A 25% glutaraldehyde (GA) aqueous solution at 4° C., 25° C., or 40° C. was added to the aqueous solutions such that the aqueous solutions contained glutaraldehyde (GA) at the corresponding concentrations listed in Table 1, followed by pipetting (see Table 1). Each solution (3.6 mL) was poured into a square dish (3 cm×3 cm×1 cm) (liquid thickness: 4 mm) and allowed to stand at the corresponding temperature for 17 hours. The thus obtained gels were separately immersed overnight in a 5M glycine aqueous solution. The gels were washed with Milli-Q water so that samples for strength measurement were obtained.

Effects of glutaraldehyde upon gelling of gelatin in HFIP and PBS were examined. At a low glutaraldehyde concentration (0.06%), gelling of gelatin was observed in HFIP, but gelling was not observed in PBS. When the glutaraldehyde concentration was increased to 0.25%, gelling was observed in both solvents.

Crosslinking in HFIP was attempted at 4° C., at which a gelatin gel was formed in PBS. In this case, it was possible to carry out uniform stirring at a glutaraldehyde concentration of up to 2.0%. In addition, it was possible to easily carry out stirring at a glutaraldehyde concentration of up to 5.0% (Table 1). It can be said that the use of HFIP as a solvent for gelling allowed stirring/gelling at low temperatures and thus it was possible to obtain a gelatin structure having a high degree of crosslinking. Even in a case in which 2,2,2-trifluoroethanol was used as a solvent instead of HFIP, similar results were obtained. In addition, when a PBS solution containing gelatin was set to 25° C., gelling of gelatin took place. Therefore, mixing of solutions and reaction were carried out at 40° C.

The strength of a crosslinked gelatin was determined with the use of a creep meter (produced by Yamaden Co., Ltd.) (RE2-33005B; plunger diameter: $\phi$=5 mm; pushing rate: 0.1 mm/s; sample thickness: 4 mm). In order to obtain the strength of crosslinked gelatin, the Young's modulus and the breaking load of crosslinked gelatin were measured. The Young's modulus was determined based on the slope of the straight line in the low strain region (strain: 0.3 or less) determined by creating a stress-distortion curve based on the stress obtained when pushing a crosslinked gelatin. In addition, the breaking load was designated as the load determined when piercing a crosslinked gelatin with a plunger so as to rupture the gelatin. At every mixing proportion, the strength of a crosslinked gelatin obtained with the use of HFIP as a solvent was greater than that of a crosslinked gelatin obtained with the use of PBS. Further, in the case of a composition of gelatin (20%) and GA (2.0%), it was impossible to carry out handling when using PBS as a solvent and thus impossible to carry out measurement. On the other hand, it was possible to carry out handling when using HFIP and it was possible to produce a crosslinked gelatin having high strength. The use of HFIP as a solvent resulted in the improvement of the strength of crosslinked gelatin to a greater extent, as compared with a case of using PBS under the same conditions. Even with the use of a high-concentration gelatin and a crosslinking agent, it was possible to carry out handling. Consequently, it can be said that a crosslinked gelatin having high strength could be produced.

TABLE 1

Effects of solvents and temperatures upon gelling of gelatin

| Solvent | HFIP/water* | GA concentration (%) | Temperature (° C.) | Occurrence or nonoccurrence of gelling | Handling | Strength |
|---|---|---|---|---|---|---|
| HFIP | 713 | 0.06 | 25 | Gelling | Easy | Low (Comparative Example) |

TABLE 1-continued

Effects of solvents and temperatures upon gelling of gelatin

| Solvent | HFIP/water* | GA concentration (%) | Temperature (° C.) | Occurrence or nonoccurrence of gelling | Handling | Strength |
|---|---|---|---|---|---|---|
| PBS | 0 | 0.06 | 40 | Solution | — | — (Comparative Example) |
| HFIP | 99 | 0.25 | 25 | Gelling | Easy | Low (Comparative Example) |
| PBS | 0 | 0.25 | 40 | Gelling | Easy | Low (Comparative Example) |
| HFIP | 24 | 1.0 | 4 | Gelling | Easy | High (the present invention) |
| PBS | 0 | 1.0 | 40 | Gelling | Possible (difficult) | High (Comparative Example) |
| HFIP | 11.5 | 2.0 | 4 | Gelling | Easy | High (the present invention) |
| PBS | 0 | 2.0 | 40 | Gelling | Impossible (impossible to stir) | High (Comparative Example) |
| HFIP | 4.0 | 5.0 | 4 | Gelling | Possible | High (the present invention) |
| PBS | 0 | 5.0 | 40 | Gelling | Impossible (impossible to stir) | High (Comparative Example) |

Gelatin concentration: 10 w/v %;
*HFIP/water (v/v)

TABLE 2

Effects of crosslinking conditions upon crosslinked gelatin strength

| Gelatin concentration (%) | Solvent | HFIP/water* | GA concentration (%) | Temperature (° C.) | Handling | Young's modulus (KPa) | Breaking load (KPa) |
|---|---|---|---|---|---|---|---|
| 15 | HFIP | 61.5 | 0.4 | 25 | Easy | 252.8 | 133 ± 32 |
| 15 | PBS | 0 | 0.4 | 40 | Easy | 49.2 | 34 ± 8 |
| 15 | HFIP | 24 | 1.0 | 25 | Easy | 366.5 | 145 ± 9 |
| 15 | PBS | 0 | 1.0 | 40 | Easy | 130.7 | 77 ± 8 |
| 20 | HFIP | 24 | 1.0 | 25 | Easy | 339.4 | 215 ± 26 |
| 20 | PBS | 0 | 1.0 | 40 | Easy | 195.1 | 136 ± 4 |
| 20 | HFIP | 11.5 | 2.0 | 25 | Easy | 422.5 | 365 ± 27 |
| 20 | PBS | 0 | 2.0 | 40 | Impossible (impossible to stir) | — | — |

*HFIP/water (v/v)

INDUSTRIAL APPLICABILITY

According to the present invention, a solvent amount can be minimized during chemical modification operations. Therefore, it is possible to cause crosslinking of a structure prepared with a biopolymer without dissolution in a solvent. In addition, according to the present invention, a crosslinked biopolymer having high strength can be produced.

The invention claimed is:

1. A method for crosslinking a biopolymer which comprises treating a biopolymer with a crosslinking agent, wherein the crosslinking agent concentration in a reaction mixture is 1.0% to 10% by weight and crosslinking is carried out in the presence of an organic fluorine compound, wherein the biopolymer is gelatin, the crosslinking agent is glutaraldehyde, and the organic fluorine compound is 1,1,1,3,3,3-hexafluoro-2-propanol.

2. The method according to claim 1, wherein the temperature for mixing before reaction is 0° C. to 30° C.

3. The method according to claim 1, wherein the temperature for mixing before reaction is 0° C. to 25° C.

4. The method according to claim 1, wherein the gelatin is a human, bovine, pig, fish or plant gelatin, or a gene recombinant gelatin.

5. A method for producing a crosslinked biopolymer, which comprises the method of claim 1.

6. A crosslinked gelatin composition, which has a Young's modulus of 200 KPa or more, wherein a crosslinking agent used for the crosslinked gelatin is glutaraldehyde.

7. The crosslinked gelatin composition according to claim 6, which has a Young's modulus of 300 KPa or more.

8. The crosslinked gelatin composition according to claim 7, wherein the gelatin is acid-treated gelatin.

9. The crosslinked gelatin composition according to claim 6, wherein the gelatin is acid-treated gelatin.

* * * * *